United States Patent
Jacobsen

(10) Patent No.: US 9,910,015 B2
(45) Date of Patent: Mar. 6, 2018

(54) SENSOR ARRAY CHIP WITH PIEZOELECTRIC TRANSDUCER INCLUDING INKJET FORMING METHOD

(71) Applicant: Texas Instruments Incorporated, Dallas, TX (US)

(72) Inventor: Stuart M. Jacobsen, Frisco, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 581 days.

(21) Appl. No.: 14/252,222

(22) Filed: Apr. 14, 2014

(65) Prior Publication Data

US 2015/0293060 A1    Oct. 15, 2015

(51) Int. Cl.
| | |
|---|---|
| G01N 29/036 | (2006.01) |
| G01N 33/487 | (2006.01) |
| G01N 29/24 | (2006.01) |
| G01N 29/02 | (2006.01) |

(52) U.S. Cl.
CPC ......... G01N 29/036 (2013.01); G01N 29/022 (2013.01); G01N 29/2437 (2013.01); G01N 33/48707 (2013.01); G01N 2291/0255 (2013.01); G01N 2291/0256 (2013.01); G01N 2291/0423 (2013.01); G01N 2291/0426 (2013.01); G01N 2291/0427 (2013.01); G01N 2291/106 (2013.01)

(58) Field of Classification Search
None
See application file for complete search history.

(56) References Cited

U.S. PATENT DOCUMENTS

| | | | |
|---|---|---|---|
| 6,024,440 A | 2/2000 | Murthy et al. | |
| 7,458,265 B2 | 12/2008 | Shih et al. | |
| 7,463,118 B2 | 12/2008 | Jacobsen | |
| 7,673,972 B2 | 3/2010 | Guan et al. | |
| 2008/0100176 A1 | 5/2008 | Haskell et al. | |
| 2011/0256687 A1 | 10/2011 | Jacobsen et al. | |

FOREIGN PATENT DOCUMENTS

WO    2009/035732    3/2009

OTHER PUBLICATIONS

Dickherber, "Design, fabrication and testing of an acoustic resonator-based biosensor for the detection of cancer biomarkers," Ph.D. Dissertation, Georgia Institute of Technology, Dec. 2008.*

* cited by examiner

Primary Examiner — Kaijiang Zhang
(74) Attorney, Agent, or Firm — Tuenlap D. Chan; Charles A. Brill; Frank D. Cimino

(57) ABSTRACT

A method of forming a functionalized sensor array includes providing a substrate having at least one sensor array chip including a plurality of sensor structures. The sensor structures include a piezoelectric layer interposed between upper and lower electrodes and positioned across an area of the sensor array chip in a spatial arrangement. An inkjet cartridge chip is also provided having a plurality of microfluidic channels including a fill side having a plurality of fill side orifices and a dispense side having a plurality of dispense nozzles, wherein two or more of the plurality of microchannels are loaded with different sensing materials, and wherein locations of the plurality of dispense nozzles are matched to the spatial arrangement. The plurality of dispense nozzles are aligned to the plurality of sensor structures, and the plurality of dispense nozzles are actuated to deposit the different sensing materials on the plurality of sensor structures.

15 Claims, 5 Drawing Sheets

SENSOR ARRAY CHIP WITH PIEZOELECTRIC TRANSDUCER INCLUDING INKJET FORMING METHOD

FIELD

Disclosed embodiments relate to integrated sensor array chips with piezoelectric transducers and methods for forming the same.

BACKGROUND

Biochips including a microarray comprising a two-dimensional grid of biosensors provide miniaturized laboratories that can perform a large number (e.g., hundreds or thousands) of simultaneous biochemical reactions. Biochips enable researchers to quickly screen large numbers of biological analytes for a variety of purposes.

The two-dimensional grid of biosensors of the microarray is an important component of a biochip. Conventionally, the biosensors are deposited on a flat substrate (e.g., chip), which may either be passive (e.g., silicon or a glass) or active, where "active" refers to the inclusion of integrated electronics and/or micromechanical devices that perform or assist in signal transduction.

Surface chemistry is typically used to covalently bind sensor molecules to the substrate. The fabrication of microarrays is generally challenging and is recognized as a major economic and technological hurdle. A significant manufacturing challenge is the process of placing each sensor at a specific position on the substrate. Various methods exist to provide sensor placement, including robotic micro-pipetting to place tiny spots of sensor (e.g., receptor) material on the substrate surface. Because each sensor is generally unique, only a few spots can be placed at a time. The low-throughput nature of this placement process results in high manufacturing costs.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments recognize there is a significant demand to develop relatively low cost miniaturized serum analysis biochip arrays for rapid and reliable point-of-care testing and monitoring. Moreover, such systems fabricated using Microelectromechanical systems (MEMS) technology can significantly enhance the quality of healthcare by offering essentially real-time measurement of a plurality of clinically relevant parameters that can be used to diagnose a plurality of different conditions to enable the assessment a patient's health.

Disclosed embodiments include methods of forming a functionalized sensor array including providing a substrate (e.g., a wafer) having at least one (and generally a large number of) sensor array chip including a plurality of sensor structures. The sensor structures include a piezoelectric layer interposed between upper and lower electrodes which are positioned across an area of the sensor array chip in a spatial arrangement. An inkjet cartridge chip is also provided having a plurality of microchannels including a fill side having a plurality of fill side orifices and a dispense side having a plurality of dispense nozzles, wherein two or more of the plurality of microchannels are loaded with different sensing materials, and wherein the locations of the dispense nozzles are matched to the spatial arrangement. The dispense nozzles are aligned to the plurality of sensor structures, and the plurality of dispense nozzles are actuated to deposit the different sensing materials on the plurality of sensor structures. The sensor structures can comprise piezoelectric cantilever based-sensors, or surface acoustic wave (SAW) sensors or bulk acoustic wave (BAW) sensors.

BRIEF DESCRIPTION OF THE DRAWINGS

Reference will now be made to the accompanying drawings, which are not necessarily drawn to scale, wherein.

DETAILED DESCRIPTION

Figure 1:
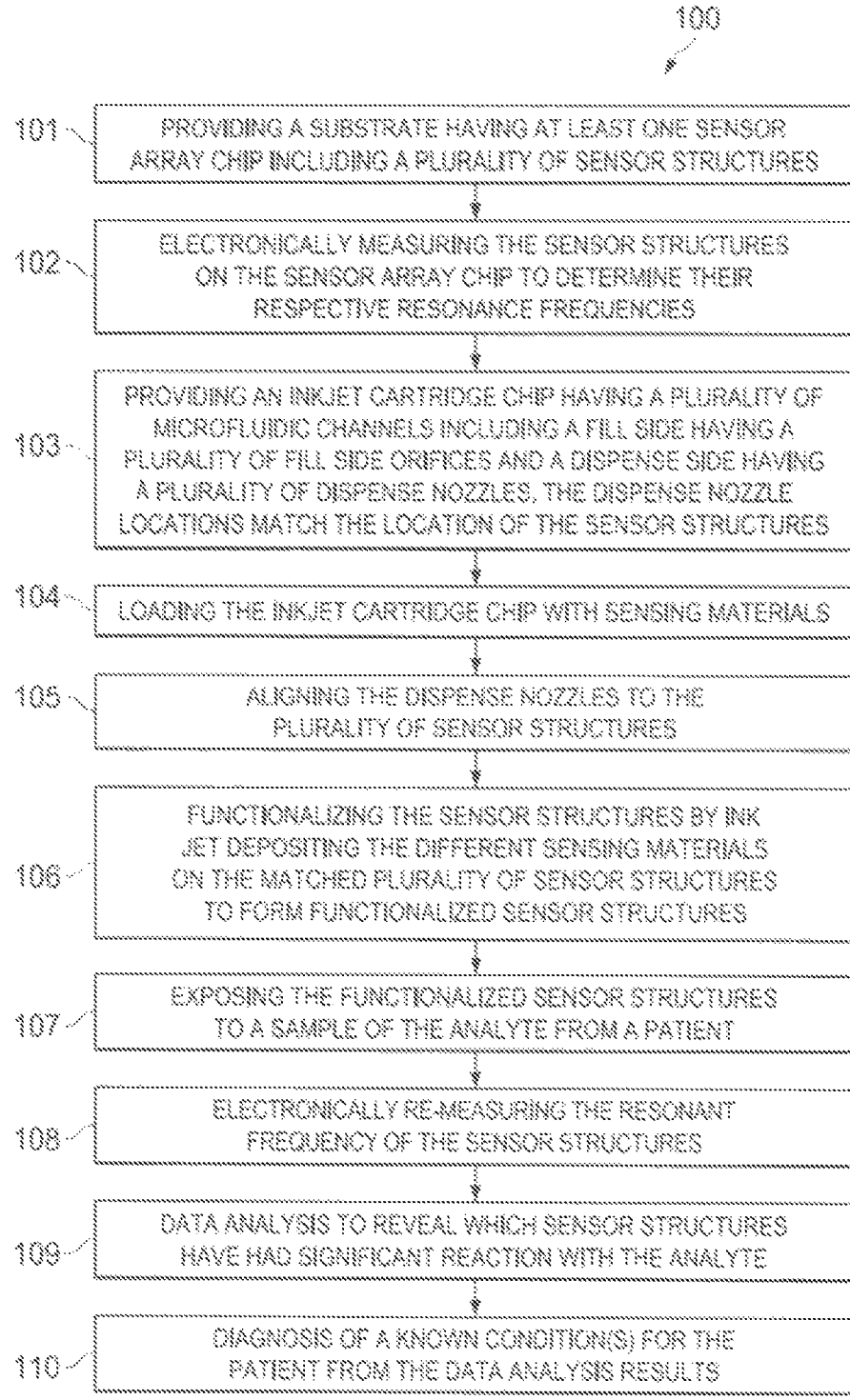
FIG. 1 is a flow chart that shows steps in an example method of forming a functionalized sensor array chip and using the functionalized sensor array chip, according to an example embodiment.

Example embodiments are described with reference to the drawings, wherein like reference numerals are used to designate similar or equivalent elements. Illustrated ordering of acts or events should not be considered as limiting, as some acts or events may occur in different order and/or concurrently with other acts or events. Furthermore, some illustrated acts or events may not be required to implement a methodology in accordance with this disclosure.

FIG. 1 is a flow chart that shows steps in an example method 100 of forming (steps 101, 103-106) and using a functionalized biosensor or chemical sensor array chip (hereafter a sensor array chip, steps 102, 107-110), according to an example embodiment. Disclosed sensor array chips include integrated circuitry thereon to provide chemical analysis systems, such as a silicon or other semiconductor substrate that provides integrated silicon microcircuit sensors. Disclosed sensor array chips can combine electrical components, sensor components and liquid channels to deliver fluids to specific sensors either for testing and electronic recording or to eject samples into a microanalysis plate. Applications for disclosed sensor array chips may include for example, microanalysis of chemicals, analysis of body fluids, sequencing of DNA and nucleotides and other medical applications realized by a low-cost biosensor and a relatively low cost method, including analyzing a sample of serum from a patient for a plurality of different conditions which can reduce cost of the testing from thousands or tens of thousands of dollars to tens of dollars.

Step 101 comprises providing a substrate (e.g., silicon wafer or glass wafer) having at least one sensor array chip including a plurality of sensor structures. In one embodiment the substrate is a wafer having a semiconductor surface including a large number (e.g., hundreds) of identical sensor array chips formed thereon. The sensor structures each includes a piezoelectric layer interposed between an upper and lower electrode that are positioned across an area of the sensor array chip in a spatial arrangement. The sensor structures can comprise piezoelectric cantilevers (see FIG. 3A described below). The sensor structures can comprise also BAW sensors (see FIG. 4A described below) including thickness shear mode (TSM) sensors or SAW sensors (see FIG. 4B described below). Disclosed sensor structures are generally configured to measure picogram to nanogram quantities of mass change on the functionalized part of the sensor structure after a region thereof has been functionalized using a picogram to nanogram quantity of sensing material (e.g., biomarker) deposited by an inkjet cartridge chip (see step 103 described below). The spatial arrangement of the sensor structures can be a periodic arrangement which provides a predetermined pitch, or be in an aperiodic arrangement.

Step 102 comprises electronically measuring the sensor structures on the sensor array chip to determine their respective resonance frequencies. The sensor array chip can include an integrated oscillator having a multiplexer at its input to measure the frequency and an analog-to-digital converter (ADC) to provide a digital frequency output. The digital frequency output data obtained is generally stored in a suitable memory for each sensor structure of the sensor array along with an identifier for the sensor structure.

Step 103 comprises providing an inkjet cartridge chip having a plurality of microfluidic channels including a fill side having a plurality of fill side orifices and a dispense side having a plurality of dispense nozzles. The inkjet cartridge chip can include microfluidic channels (or microchannels) that allow filling at the top (fill side) through large orifices, which are then reduced in size getting down to small nozzles on the dispense side of the inkjet cartridge chip. The plurality of dispense nozzles are generally thus smaller in area as compared to an area of the fill side orifices, such as by a factor of at least 10.

An inkjet cartridge chip having large fill side orifices and small nozzles (e.g., 10 times smaller) can be realized using the subject matter disclosed in application Pub. U.S. Pat. App. No. 20110256687 (to Jacobsen, the same inventor herein) entitled "Method for Fabricating Through Substrate Microchannels", which is incorporated by reference herein. A dispense actuator can control dispensing of the sensing materials from the microchannels.

The final assembled cartridge generally includes two main components, an upper component generally comprising plastic which contains fill orifices, and a lower component which is made of a silicon or another semiconductor material that contains the dispense nozzles. The upper component generally includes molded plastic channels that transport the individual sensing material to their respected targets on the lower component. The lower component is generally bonded to the upper component using epoxy adhesive or other methods familiar to those who practice in the art of inkjet cartridge manufacturing. In some situations it may be beneficial to devote a larger portion of the lower substrate area to having only the function of containing receiving orifices that mate with the upper component.

Microchannels in the lower component further narrow and focus the pathways of the plurality of analyte fluids toward the area of the lower substrate that contains the dispense nozzles which provide jetting areas. An advantage of this arrangement is that this allows the functionalized sensor array on which the analyte will be jetted to have a small area which results in lower cost for the intended one-time-use. Each dispense nozzle contains its own dispensing element, being a miniature heater in the case of a thermal ejection device or alternatively a piezoelectric dispensing device.

Step 104 comprises loading the inkjet cartridge chip with sensing materials. Two or more of the plurality of microchannels are loaded with different sensing materials, and generally collectively the sensor structures are loaded with tens, hundreds or thousands of different sensing materials. Loading can be performed through conventional needle fill (generally on the scale of micro-liters, for example, with biomarkers such as test lipids or antibodies). As known in the art of inkjets, leakage of the sensing materials before the intended dispense is prevented by the liquid meniscus at the dispense nozzle which holds back the reservoir (in inkjet vernacular this is generally called "drool").

The inkjet chip is thus configured so that a single cartridge of fluid is interfaced to the inkjet cartridge chip that delivers tens, hundreds or thousands of different biomarkers through a series of microfluidic channels. As noted above, the locations of the dispense nozzles are matched to the spatial arrangement of sensor structures.

Step 105 comprises aligning the dispense nozzles to the plurality of sensor structures. The aligning can comprise alignment marks as known in IC fabrication or other known alignment structures or techniques.

Step 106 comprises a functionalization step comprising actuating the plurality of dispense nozzles to deposit the different sensing materials on the matched plurality of sensor structures to form functionalized sensor structures. The deposition can be performed through a single printing step thus being essentially simultaneous. The ejection of sensing materials is generally performed either by thermal pulse (for a thermal inkjet printer) or a mechanical pulse (for a piezoelectric inkjet printer). Each dispense nozzle can generally have its own unique miniature heater (for the case of a thermal inkjet printer) that is individually addressed. Each pulse can deliver a precise ejection of nano-liter (or even pico-liter) sized drop of sensing material. The functionalization step generally takes of the order of seconds to tens of seconds, with tens, hundreds or thousands of sensor structures being functionalized.

Step 107 comprises further processing the sensor array chip by exposing all the functionalized sensor structures to a single sample of the analyte (e.g., a body fluid such as saliva, blood etc.). The sensing material (e.g., biomarkers) present on the functionalized sensor structures (e.g., tips for cantilever sensors) chemically react with the constituents of the serum. One or more chemical reactions can take place, which adds mass, and then a drying step generally occurs. Step 108 comprises electronically re-measuring the resonant frequency of the sensor structures and the resonant frequency data generated is stored.

Step 109 comprises data analysis which reveals which sensor structures have had significant reaction with the analyte by calculating a mass change through the change in resonant frequency due to analyte exposure. If a particular biomarker has shown a positive response, the mass changes and even very small changes in mass as small as one atomic monolayer can generally be detected as a change in resonant frequency. All of this information can be optionally sent to a handheld computer to which the sensor array chip is interfaced and a report can be produced on the serum, such as to a medical professional, which can provide a status on the patient to enable a diagnosis of known (i.e., existing) conditions in step 110.

Advantage of disclosed methods include tens or hundreds of different medical tests can be carried out essentially simultaneously. The sensor array chip can be functionalized at the point of care in situ, so that the functionalized sensor structures do not have time to degrade through long shelf-time storage, and can be promptly used by exposing the sensor structures on freshly prepared functionalized sensor array chip to a sample of serum from a patient for example. Results can be available within minutes. As noted above, a set of tests normally costing thousands or tens of thousands of dollars can be performed for tens of dollars.

Figure 2A:
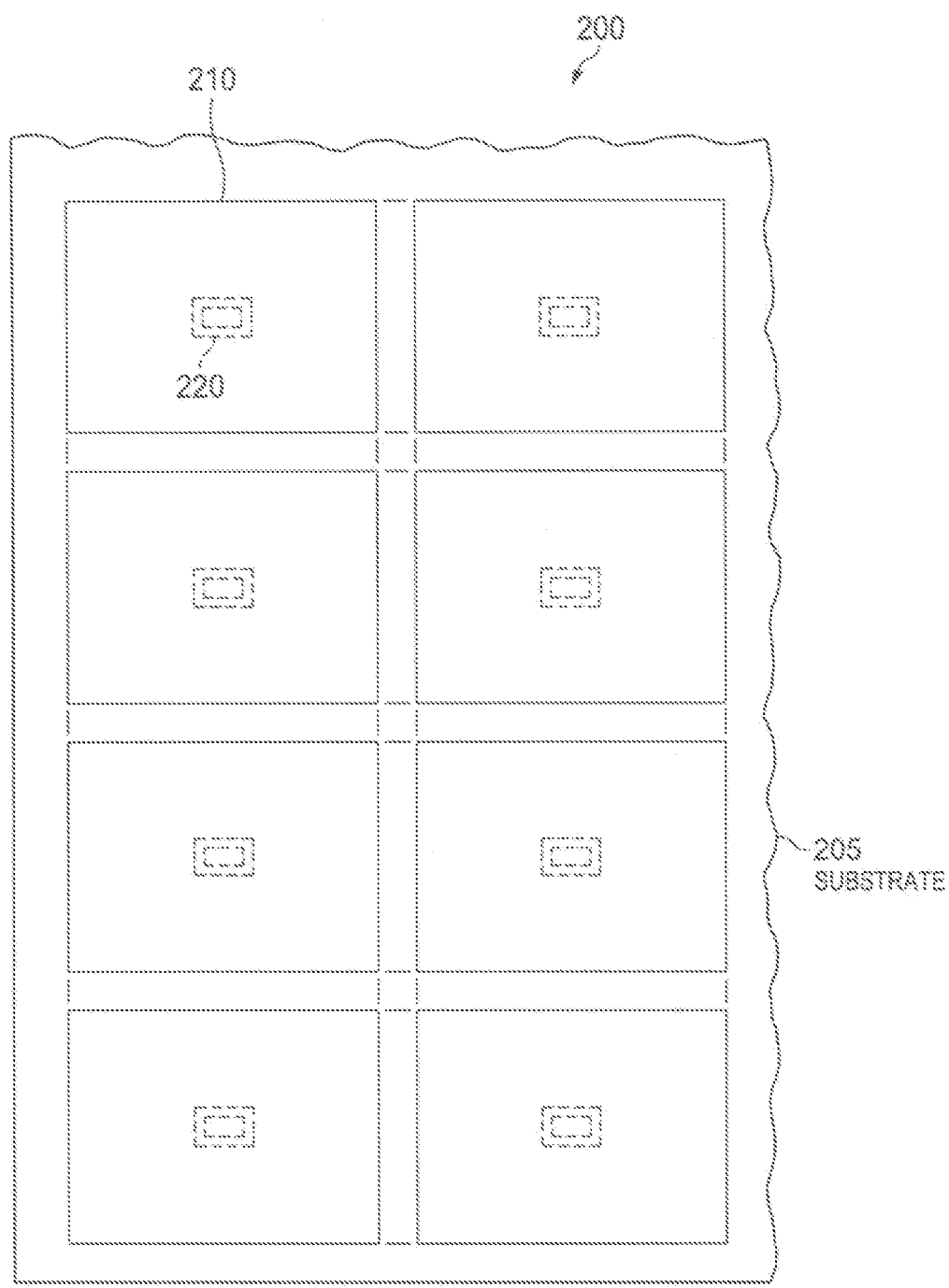
FIG. 2A is a depiction of an example inkjet cartridge chip having a plurality of microchannels including a fill side having a plurality of fill side orifices and a dispense side having a plurality of dispense nozzles, wherein two or more of the microchannels are loaded with different sensing materials, and wherein locations of the dispense nozzles are matched to the spatial arrangement of sensor structures on a sensor array chip, according to an example embodiment.

FIG. 2A is a depiction of an example IC-based inkjet cartridge chip 200 built on a substrate 205 having a plurality of microchannels including a fill side having a plurality of fill side orifices 210 and a dispense side having a plurality of dispense nozzles 220. As disclosed above, two or more of the microchannels are loaded with different sensing materials (e.g., biomarkers such as lipids or antibodies) and the locations of the dispense nozzles 220 are matched to the spatial arrangement of the sensor structures on the sensor array chip (see FIG. 2B described below for a matching sensor structure spatial arrangement).

Figure 2B:
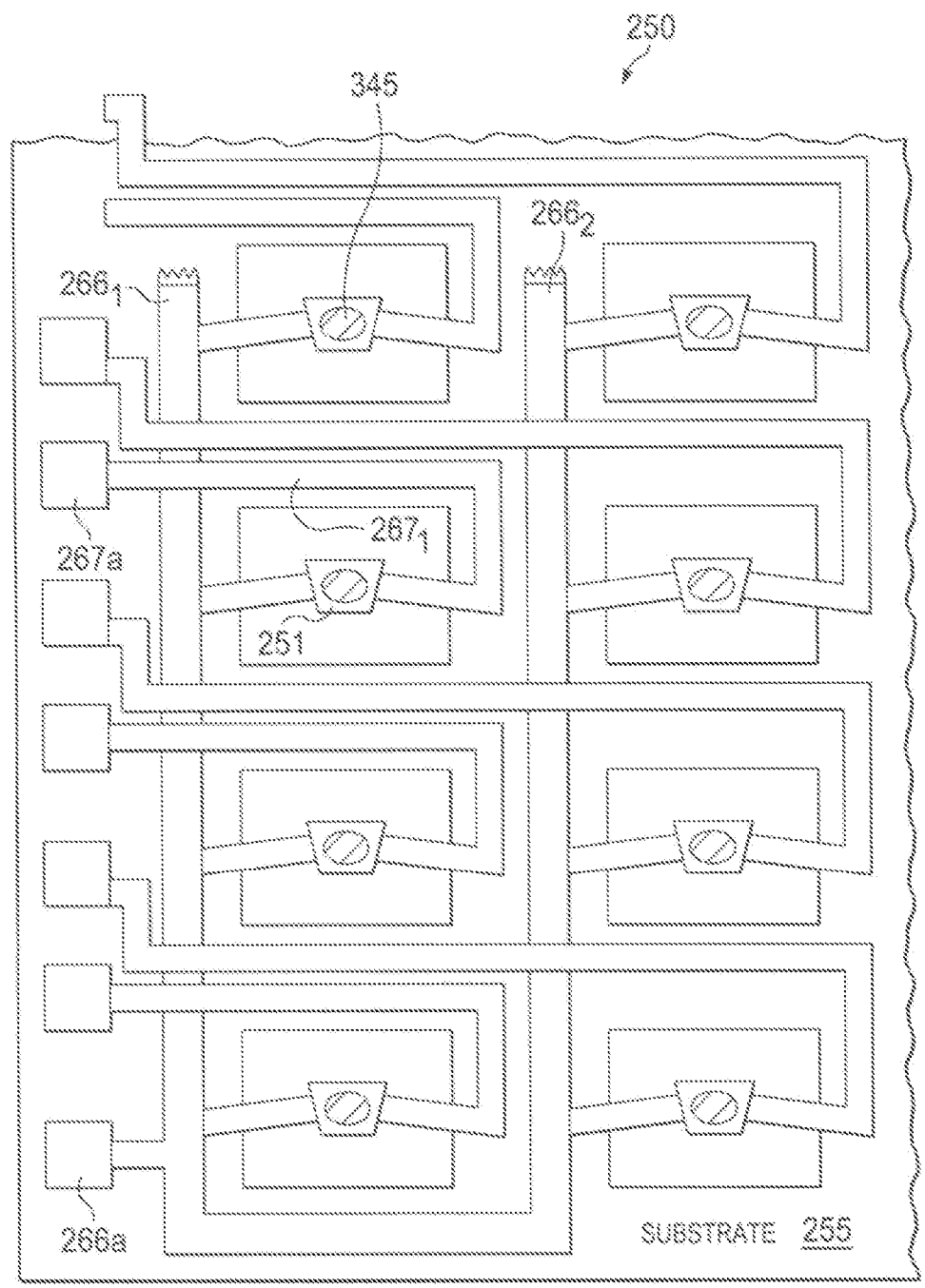
FIG. 2B is a depiction of an example sensor array chip shown including a plurality of sensor structures, where the sensor structures include a piezoelectric layer interposed between upper and lower electrodes positioned across an area of the sensor array chip in a spatial arrangement that matches a spatial arrangement of the plurality of dispense nozzles shown in FIG. 2A, according to an example embodiment.

FIG. 2B is a depiction of an IC-based sensor array chip 250 comprising a substrate 255 with the lower left corner of sensor array chip 250 shown having a plurality of functionalized sensor structures with 8 sensor structures shown including sensor structure 251. A plurality of sensor array chips, such as sensor array chip 250, are generally formed on a common substrate before being singulated. The sensor structures include a piezoelectric layer interposed between an upper electrode and a lower electrodes (see, e.g., the piezoelectric cantilever shown in FIG. 3A described below) which are positioned across an area of the sensor array chip 250 in a spatial arrangement that matches a spatial arrangement of the plurality of dispense nozzles shown in FIG. 2A. The shape of the sensor structures are each shown as being apodized (no parallel lines) to help avoid spurious resonances. Each sensor structure is shown having a functionalized area comprising a sensing material 345 which as described above can be deposited by the inkjet cartridge described above.

The upper electrode is shown routed to a unique signal bondpad for each sensor structure. The sensor array chip 250 can then be bonded out (e.g., wirebond or tab-bond) to electronics including an oscillator to allow interrogating each sensor structure for frequency before and after the sensor array chip 250 has been exposed to an analyte. Changes in frequency allows detection of changes in mass caused by chemical reaction of the functionalized sensor structures with the analyte. Ground bus line $266_1$ and $266_2$ couple the bottom electrode of all sensors structure to a common input/output (I/O) ground pad shown as 266a. Top electrode traces are provide for each sensor structure including trace $267_1$ to connect the top electrode of sensor structure 251 to a dedicated I/O pad shown as 267a.

Although not shown in FIG. 2B the sensor array chip 250 can include an integrated oscillator. Sensor array chip 250 can also include a multiplexer (MUX) before the oscillator to allow a single oscillator to allow measuring the respective resonant frequencies from the respective sensor structures. In addition, an analog-to-digital converter (ADC) can be provided to digitize the output from the oscillator to provide a digital frequency output.

Figure 3A:
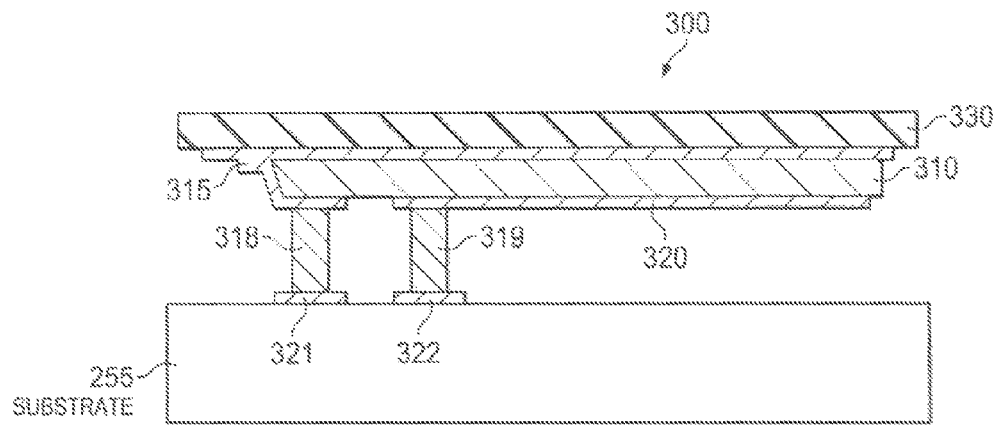
FIG. 3A is a cross sectional depiction of an example sensor structure comprising a piezoelectric cantilever before functionalization with a sensing material, according to an example embodiment.

FIG. 3A is a cross sectional depiction of a sensor structure 300 comprising a piezoelectric cantilever before functionalization with sensing materials. Sensor structure 300 include a piezoelectric layer 310 interposed between an upper electrode 315 and a lower electrode 320. The upper electrode 315 and a lower electrode 320 are shown electrically connected by metal comprising posts 318 and 319 to pads 321 and 322. A top layer 330 comprises a dielectric material which functions as protective layer is shown over the upper electrode 315. Top layer 330 can comprise silicon nitride, silicon oxide or silicon oxynitride.

The piezoelectric layer 310 can comprise aluminum nitride (AlN) or other materials such as zinc oxide (ZnO), lead zirconate titanate (PZT), quartz ($SiO_2$) or barium titanate ($BaTiO_3$) and the like. For example, an AlN layer can be reactively sputter deposited with nitrogen gas using a process yielding a low stress, dense layer employing a c-axis orientation. The thickness of the piezoelectric layer 310 can be in the range from about 0.1 μm to about 10 μm.

Figure 3B:
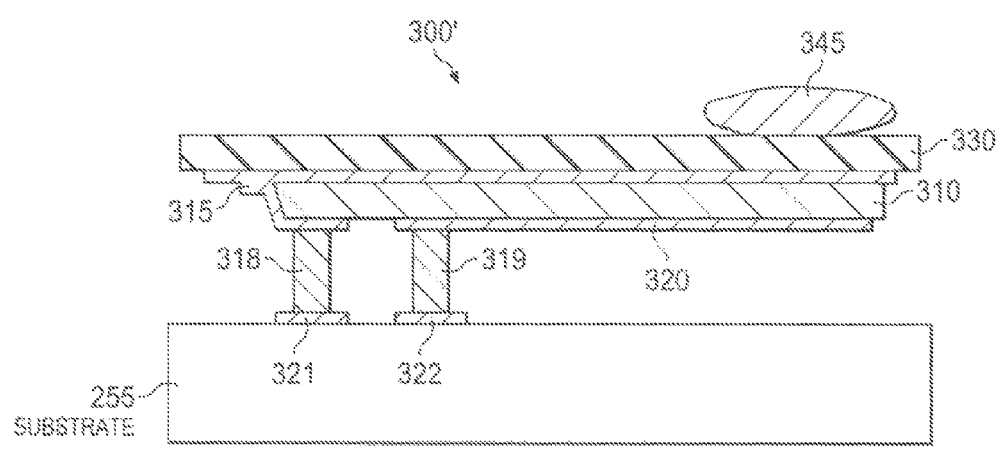
FIG. 3B is a cross sectional depiction of the sensor structure comprising the piezoelectric cantilever shown in FIG. 3A after sensing material (e.g., biomarker) deposition to provide functionalization by a disclosed inkjet cartridge chip, according to an example embodiment.
Figure 3C:
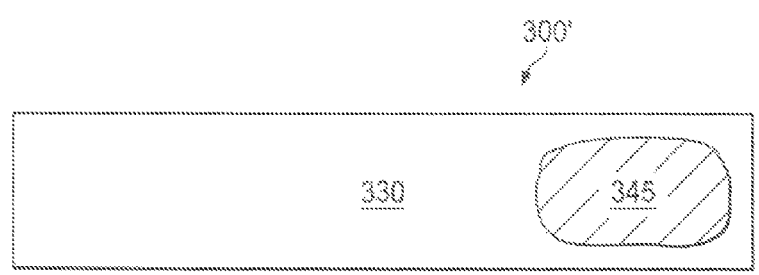
FIG. 3C is a top view of the sensor structure comprising the functionalized piezoelectric cantilever shown in FIG. 3B.

FIG. 3B is a cross sectional depiction of the sensor structure comprising the piezoelectric cantilever shown in FIG. 3A after being functionalized (functionalized sensor structure 300') with a sensing material deposited by a disclosed inkjet cartridge chip. The sensing material (e.g., biomarker) is shown as 345 and is deposited on the top layer 330. FIG. 3C is a top view of the functionalized sensor structure 300' comprising the piezoelectric cantilever shown in FIG. 3B having the sensing material 345 on the top layer 330.

Figure 4A:
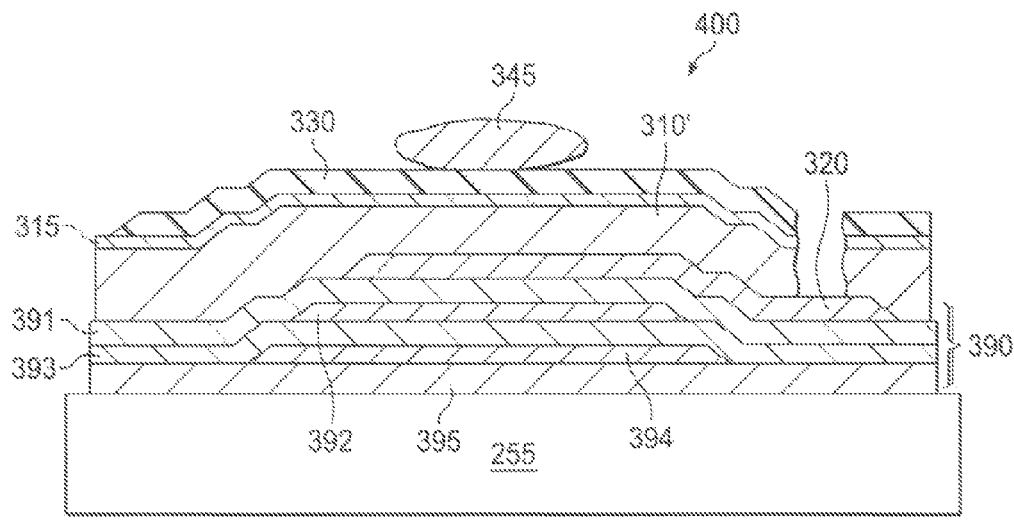
FIG. 4A is a cross sectional depiction of an example sensor structure comprising a BAW sensor functionalized with a sensing material thereon.

FIG. 4A is a cross sectional depiction of a partially completed sensor structure comprising a BAW sensor 400 that implements a Solidly Mounted Resonator (SMR) 320, 310', 330 functionalized with a sensing material 345 thereon. BAW sensor 400 provides a solidly mounted piezoelectric layer 310' as compared to the piezoelectric layer 310 which is suspended in the cantilever sensor embodiment shown in FIGS. 3A-C making this embodiment generally more mechanically robust, so that there is little risk of mechanical damage in any of the standard backend processes used including dicing, assembly and packaging.

An acoustic Bragg reflector is located between the SMR 320, 310', 330 and the substrate 255. The acoustic Bragg reflector includes 390 includes a plurality of layers 391 to 395. Layers 391, 393, and 395 of the acoustic Bragg reflector 390 are layers with high acoustic impedance and layers 392, 394 are layers with low acoustic impedance. The thickness of each of these layers 391 to 395 is fixed to be about one quarter wavelength of the resonant frequency. The greater the number of alternating layers present in the acoustic Bragg reflector 390 the greater is the efficiency of the reflector. The efficiency of the acoustic Bragg reflector is also dependant on the mismatch between the acoustic impedances. The greater the difference in acoustic impedance between the low and high acoustic impedance materials, the more efficient the reflector.

As described above, adding material from an analyte solution to sensing material 345 on the top layer 330 causes a resonant frequency shift to take place. When the resonant frequency is about 1 GHz even the addition of 1 atomic monolayer from the analyte can cause a measurable change in resonant frequency of typically at least one part per million, such as 1 kHz to several MHz. As disclosed above, the top layer 330 for a plurality of sensor structures can be selectively functionalized with different sensing materials using an inkjet printer chip having positional matched dispense nozzles.

Figure 4B:
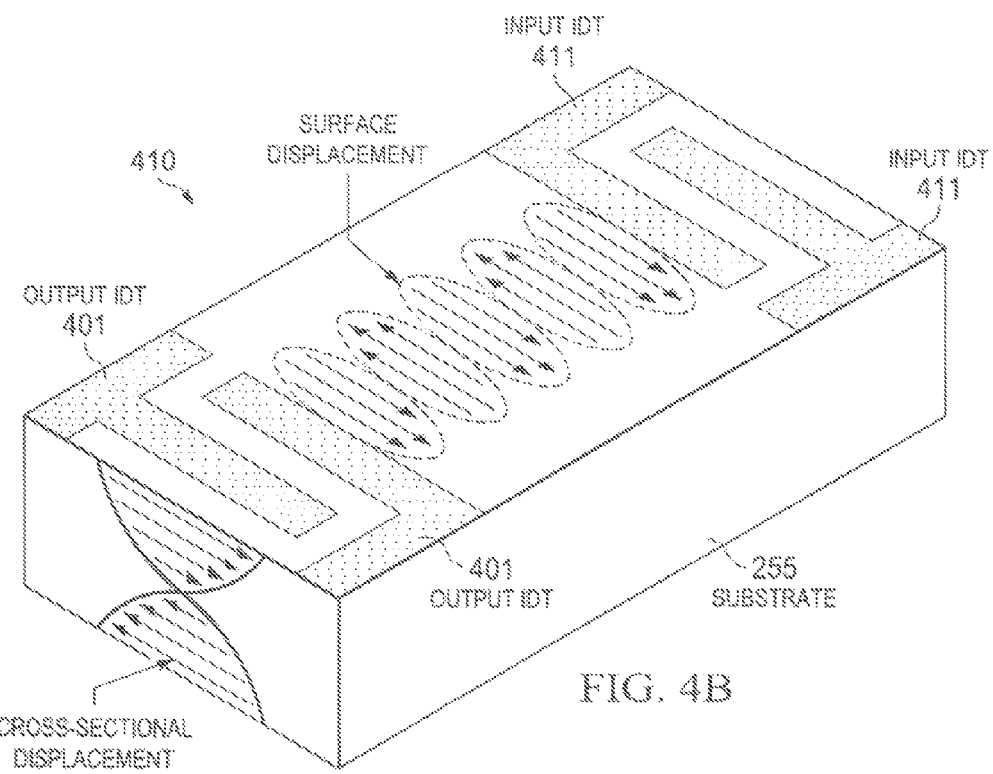
FIG. 4B is a cross sectional depiction of an example sensor structure comprising a SAW sensor.

FIG. 4B is a cross sectional depiction of the sensor structure comprising a SAW sensor shown as a shear horizontal acoustic plate mode (SHAPM) sensor 410. The SHAPM sensor 410 includes an input interdigitated transducer (IDT) 411 and output IDT 401. Although not shown functionalized in FIG. 4B, to functionalize the SHAPM sensor 410 a sensing material would be deposited in the region identified in FIG. 4B having "surface displacement". In this embodiment the substrate 255 is a piezoelectric substrate.

Disclosed sensor arrays can reliably measure a wide variety of clinically relevant parameters at the typical concentrations observed in human blood or other body fluid with adequate accuracy and precision. Furthermore, disclosed the sensor arrays are fully integrated, generally being on the same low-cost substrate as the remaining biochip for ease of integration and low-cost.

Disclosed sensor arrays thus realize a fully integrated, disposable sensor array biochip that can be deployed for point-of-care testing (POCT) applications, which satisfy several helpful criteria. Some of these criteria include (a) low cost per disposable sensor array biochip wherein the low cost is obtained by using low-cost biocompatible substrate materials such as silicon or glass; (b) a low cost, mass producible fabrication process for the sensor array biochips wherein the high manufacturing volumes reduce the per device cost; (c) fully-integrated sampling capability, the use of which allows for the sensor array biochip to directly acquire serum samples; (d) an integrated sensor array biochip wherein the functionalized sensor array chip is fabricated on the same substrate as the rest of the sensor array chip to allow integration with the rest of the sensor array chip including readout electronics; and (e) a low-cost, high volume compatible fabrication process for the sensor array biochip wherein the high volume manufacturing drives down the cost of the each sensor array chip.

Those skilled in the art to which this disclosure relates will appreciate that many other embodiments and variations of embodiments are possible within the scope of the claimed invention, and further additions, deletions, substitutions and modifications may be made to the described embodiments without departing from the scope of this disclosure. For example, although medical diagnostic testing for human patients is disclosed, disclosed embodiments can be also used for animal diagnostic testing.

The invention claimed is:

1. A medical diagnostic kit combination, comprising:
a sensor array chip including sensor structures, each of the sensor structures including: a piezoelectric layer interposed between upper and lower electrodes, and a dielectric layer above said upper electrode, said sensor structures positioned across an area of said sensor array chip in a spatial arrangement, and
an inkjet cartridge chip having microchannels including a fill side having fill side orifices and a dispense side having dispense nozzles, wherein two or more of said microchannels are loaded with different sensing materials, and wherein locations of said dispense nozzles are matched to said spatial arrangement.

2. The medical diagnostic kit combination of claim 1, wherein said dispense nozzles are smaller in area as compared to an area of said fill side orifices.

3. The medical diagnostic kit combination of claim 1, wherein said spatial arrangement is a periodic arrangement having a predetermined pitch.

4. The medical diagnostic kit combination of claim 1, wherein said sensor structures each includes a cantilever.

5. The medical diagnostic kit combination of claim 1, wherein said sensor structures each includes a bulk acoustic wave (BAW) sensor.

6. The medical diagnostic kit combination of claim 5, wherein said BAW sensor comprises a thickness shear mode (TSM) sensor.

7. A method of forming a functionalized sensor array, comprising:
providing a substrate having at least one sensor array chip including sensor structures, each of the sensor structures including: a piezoelectric layer interposed between upper and lower electrodes, and a dielectric layer above said upper electrode, said sensor structures positioned across an area of said sensor array chip in a spatial arrangement;
providing an inkjet cartridge chip having a plurality of microchannels including a fill side having a plurality of fill side orifices and a dispense side having a plurality of dispense nozzles, wherein two or more of said plurality of microchannels are loaded with different sensing materials, and wherein locations of said plurality of dispense nozzles are matched to said spatial arrangement;
aligning said plurality of dispense nozzles to said sensor structures; and
actuating said plurality of dispense nozzles to deposit said different sensing materials on said sensor structures.

8. The method of claim 1, wherein said plurality of dispense nozzles are smaller in area as compared to an area of said plurality of fill side orifices.

9. The method of claim 1, wherein said actuating said plurality of dispense nozzles is performed simultaneously.

10. The method of claim 1, wherein said spatial arrangement is a periodic arrangement which provides a predetermined pitch.

11. The method of claim 1, wherein said sensor structures each includes a cantilever.

12. The method of claim 1, wherein said sensor structures each includes a bulk acoustic wave (BAW) sensor.

13. The method of claim 12, wherein said BAW sensor comprises a thickness shear mode (TSM) sensor.

14. The method of claim 7, further comprising:
electronically measuring said sensor structures to determine an initial resonant frequency and initial resonant frequency data is stored for each of said sensor structures;
exposing said sensor structures to a sample of an analyte;
electronically re-measuring said sensor structures to determine a post exposure resonant frequency and post exposure resonant frequency data is stored;
analyzing a change in resonant frequency from a difference between said initial resonant frequency data and said post exposure resonant frequency data to identify which of said sensor structures have had a reaction with said analyte; and diagnosing of a medical condition from said analyzing.

15. The method of claim 1, wherein said substrate has a plurality of said sensor array chip, further comprising translating said inkjet cartridge chip from a first of said plurality of sensor array chip to a second of said plurality of sensor array chip (second sensor array chip), and:

aligning said plurality of dispense nozzles to said sensor structures on said second sensor array chip, and actuating said plurality of dispense nozzles to simultaneously deposit said different sensing materials on said sensor structures of said second sensor array chip.

\* \* \* \* \*